United States Patent
Baeuerle et al.

(10) Patent No.: US 9,671,375 B2
(45) Date of Patent: Jun. 6, 2017

(54) FLUIDIC CHIP WITH DISPLACABLE PATTERNED LAYER FOR DETECTING FLUID PRESSURE

(75) Inventors: Martin Baeuerle, Waldbronn (DE); Konstantin Choikhet, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 415 days.

(21) Appl. No.: 14/344,113

(22) PCT Filed: Sep. 15, 2011

(86) PCT No.: PCT/EP2011/066052
§ 371 (c)(1),
(2), (4) Date: Mar. 11, 2014

(87) PCT Pub. No.: WO2013/037414
PCT Pub. Date: Mar. 21, 2013

(65) Prior Publication Data
US 2015/0000416 A1    Jan. 1, 2015

(51) Int. Cl.
*G01N 30/32* (2006.01)
*B01L 3/00* (2006.01)
(Continued)

(52) U.S. Cl.
CPC .............. *G01N 30/32* (2013.01); *B01D 15/10* (2013.01); *B01D 53/025* (2013.01); *B01D 57/02* (2013.01); *B01L 3/5027* (2013.01); *G01L 13/023* (2013.01); *G01L 13/06* (2013.01); *G01L 27/002* (2013.01); *G01N 30/36* (2013.01); *B01L 2200/146* (2013.01);
(Continued)

(58) Field of Classification Search
CPC ........ G01N 30/32; G01N 30/36; B01D 15/10; B01D 53/025; B01D 57/02; B01L 3/5027; G01L 13/023; G01L 13/03; G01L 27/002
USPC .................................................. 73/708, 700
See application file for complete search history.

(56) References Cited

U.S. PATENT DOCUMENTS 3,985,021 A    10/1976   Achener et al.
5,163,329 A    11/1992   Shimaoka et al.
(Continued)

FOREIGN PATENT DOCUMENTS

CN    1936412 A    3/2007
DE    19832681 A1   2/2000
(Continued)

OTHER PUBLICATIONS

Chinese Office Action for CN 201180073493.6 mailed on Feb. 17, 2015.
(Continued)

*Primary Examiner* — Lisa Caputo
*Assistant Examiner* — Nathaniel T Woodward

(57) ABSTRACT

A fluidic chip device configured for processing a fluid, wherein the fluidic chip device comprises a plurality of layers laminated to one another, wherein at least a part of the layers comprises a patterned section of an alternating sequence of bars and fluidic channels for conducting the fluid under pressure, the patterned section being configured for being displaceable in response to the pressure, and a pressure detector responding to the displacement of the patterned section by generating a detector signal being indicative of a value of the pressure.

21 Claims, 10 Drawing Sheets

(51) Int. Cl.
*B01D 15/10* (2006.01)
*B01D 53/02* (2006.01)
*B01D 57/02* (2006.01)
*G01L 13/02* (2006.01)
*G01L 13/06* (2006.01)
*G01L 27/00* (2006.01)
*G01N 30/36* (2006.01)
*G01N 30/60* (2006.01)

(52) U.S. Cl.
CPC ............ *B01L 2300/0663* (2013.01); *B01L 2300/0816* (2013.01); *B01L 2300/14* (2013.01); *B01L 2400/0487* (2013.01); *G01N 30/6095* (2013.01); *G01N 2030/326* (2013.01)

(56) References Cited

U.S. PATENT DOCUMENTS

| | | |
|---|---|---|
| 5,645,684 A | 7/1997 | Keller |
| 7,252,006 B2 | 8/2007 | Tai et al. |
| 7,509,869 B2 | 3/2009 | Liu et al. |
| 2010/0017135 A1* | 1/2010 | Mostowfi .......... B01L 3/502784 702/8 |

FOREIGN PATENT DOCUMENTS

| | | |
|---|---|---|
| WO | 2004085063 A2 | 10/2004 |
| WO | 2007014336 A1 | 2/2007 |
| WO | 2011013111 A1 | 2/2011 |

OTHER PUBLICATIONS

International Search Report and Written Opinion dated May 31, 2012, for corresponding patent application PCT/EP2011/066052 filed Sep. 15, 2011, and references cited therein.

Cho, S.T. et al.; "An ultrasensitive silicon pressure-based flowmeter"; Dec. 3, 1989; pp. 499-502, XP010079905.

Kohl, M.J. et al.; "A microfluidic experimental platform with internal pressure measurements"; Sensors and Actuators A, Elsevier Sequoia S.A., Lausanne, CH, vol. 118, No. 2, Feb. 28, 2005, pp. 212-221, XP025324936.

* cited by examiner

FLUIDIC CHIP WITH DISPLACABLE PATTERNED LAYER FOR DETECTING FLUID PRESSURE

RELATED APPLICATIONS

This application is the national stage of International Application No. PCT/EP2011/066052, filed Sep. 15, 2011, titled "FLUIDIC CHIP WITH DISPLACABLE PATTERNED LAYER FOR DETECTING FLUID PRESSURE," the content of which is incorporated herein by reference in its entirety.

BACKGROUND ART

The present invention relates to a fluidic chip device and to a method.

Many technical fields require pressure measurement. For instance, such systems are disclosed in U.S. Pat. No. 3,985,021, U.S. Pat. No. 5,645,684, DE 19832681, U.S. Pat. No. 7,252,006, WO 2007/014336, U.S. Pat. No. 7,509,869, WO 2011/013111, or M. J. Kohl, S. I. Abdel-Khalik, S. M. Jeter, D. L. Sadowski, "A microfluidic experimental platform with internal pressure measurements", Sensors and Actuators A 118 (2005), pages, 212 to 221.

Also in liquid chromatography, pressure measurement of a fluid may be desired. In liquid chromatography, a fluidic analyte may be pumped through a column comprising a material which is capable of separating different components of the fluidic analyte. Such a material, so-called beads which may comprise silica gel, may be filled into a column tube which may be connected to other elements (like a control unit, containers including sample and/or buffers). Part of such a chromatography arrangement may be integrated in a fluidic chip device.

US 2009/238722 discloses such a fluidic chip device configured for processing a fluidic sample, the fluidic chip device comprising a substrate having a fluidic conduit for conducting the fluidic sample under pressure, and two reinforcing structures between which the substrate is arranged, wherein the two reinforcing structures are connected to one another to reinforce pressure resistance of the substrate.

Operation of a liquid chromatography system may involve the application of a high pressure such as 1000 bar or more. This may be a challenge for proper control of the liquid chromatography system.

DISCLOSURE

It is an object of the invention to provide an efficient fluidic chip device being properly controllable even under high-pressure applications.

According to an exemplary embodiment of the present invention, a fluidic chip device configured for processing a fluid is provided, wherein the fluidic chip device comprises a plurality of layers laminated to one another, wherein at least a part of the layers comprises a patterned section of an alternating sequence of bars and fluidic channels for conducting the fluid under pressure, the patterned section being configured for being displaceable in response to the pressure, and a pressure detector configured for responding to the displacement of the patterned section by generating a detector signal being indicative of a value of the pressure.

According to another exemplary embodiment, a method of detecting information (such as data) indicative of a pressure value of a fluid flowing in a fluidic chip device configured for processing the fluid is provided, the fluidic chip device comprising a plurality of layers laminated to one another and a pressure detector being at least partially integrated within the plurality of layers, wherein at least a part of the layers comprises a patterned section of an alternating sequence of bars and fluidic channels, wherein the method comprises enabling displacement of the patterned section in response to a pressure applied by conducting the fluid under the pressure through the fluidic channels, and detecting the displacement of the patterned section by generating, by the pressure detector, a detector signal being indicative of a value of the pressure.

In the context of this application, the term "fluidic chip device" may particularly denote a (for instance flat and planar or basically planar) chip-like configuration which has provisions to perform a predefined task with a supplied fluid.

In the context of this application, the term "processing" may particularly denote any process performed with the fluid or sample. This may include a mere conduction of the fluidic sample through the fluidic chip device (for instance when the fluidic chip device is a connection piece). It is however also possible that the processing is an active procedure such as a sample separation, for example using a chromatographic column or an electrophoresis separation unit.

In the context of this application, the term "patterned section of an alternating sequence of bars and fluidic channels" may particularly denote a structured layer portion (for instance a structured metallic portion) of a layer which has various fluidic channel sections (at positions of the patterned layer at which layer material has been removed by the patterning procedure) fluidically separated from one another by various bar sections (at positions of the patterned layer at which layer material has not been removed by the patterning procedure). A bar section may hereby denote any material portion of the patterned layer regardless of a certain shape.

In the context of this application, the term "displaceable" may particularly denote that the patterned section is mounted freely within its layer and relative to the other layers so that it will be moved by the pressure exerted by the pressurized fluid in the fluidic channels.

In the context of this application, the term "detector signal" may particularly denote any output of the detector measurable as a result of the displacement and being characteristic for a quantity of the displacement and hence of the fluid pressure.

In the context of this application, the term "fluid" may particularly denote any liquid, any gas, any mixture of liquid and gas, optionally comprising solid particles. Particularly, analytes in liquid chromatography are not necessarily liquids, but can be dissolved solids or dissolved gases.

In the context of this application, the term "laminated" may particularly denote the result of the creation of a laminate by bonding sheets of material, particularly using a bonding material or bonding agent. Lamination may be performed so that a number of preformed layers are fixedly connected to one another with a direct contact between adjacent layers (with exception of a very thin layer of the bonding agent, if any) so that the layers cannot be separated from one another without destroying the stack of laminated layers. Such a fixed connection may be achieved by, for instance, gluing, pressing, welding, bonding, remelting and solidifying, or a chemical reaction.

According to an exemplary embodiment of the invention, a stack of layers laminated to one another has at least one layer with at least a section thereof being structured so that fluid channels (defining a flow path along which a fluid may flow within the fluidic chip device) alternate with bars (i.e. physical structures separating or fluidically decoupling the various fluidic channels from one another). By such a patterning, the material of the layer is weakened with regard to its stability so that a fluid flowing under a high pressure (of for instance 1200 bar in a liquid chromatography application) will significantly displace the patterned section, i.e. will move the bars in a specific manner characteristic for the pressure. By integrating a pressure detector in this layer stack sensing the displacement of the patterned section, pressure values may be detected accurately in an interior of the fluidic chip device which is of high value for a precise control and operation of the fluidic chip device.

Next, further exemplary embodiments of the fluidic chip device will be explained. However, these embodiments also apply to the method.

In an embodiment, the fluidic chip device comprises a further patterned section of an alternating sequence of further bars and further fluidic channels for conducting a further fluid (which may be the same fluid as or another fluid than the one conducted through the patterned section) under pressure (which may be the same pressure as or another pressure than the pressure of the fluid conducted through the patterned section), wherein the further patterned section is configured for being displaceable in response to the pressure of the further fluid. The pressure detector can then be configured for responding to the displacement of the further patterned section by generating a further detector signal being indicative of a value of the pressure of the further fluid. A differential pressure determining unit may be configured for determining information related to a pressure difference between the fluid and the further fluid based on the detector signal and based on the further detector signal. In such an embodiment, pressure differences between fluidic channels may be measured. Hence, if the pressure into fluid channels is the same, the differential pressure determining unit will not output any signal deviating from zero. However, in case of a pressure difference, a signal indicative of this pressure difference only will be output. Therefore, it is for instance possible by measuring with such a differential technique two different sections of a fluidic channel (for instance upstream and downstream of a processing element) to obtain a quantitative measure for the pressure drop at the processing element. This may, in turn, allow to derive whether the functioning of the processing element is proper or not. Furthermore, such a differential measurement has an even higher accuracy than an absolute pressure measurement with only one patterned section.

In an embodiment, the further patterned section is assigned to another part of the layers than the patterned section. For instance, the patterned section and the further patterned section may be arranged in adjacent layers parallel to one another. Hence, pressure differences between fluid or fluids flowing through different layers may be detected.

In an alternative embodiment, the further patterned section is assigned to the same layers as the patterned section. For instance, the patterned section and the further patterned section may both be partially arranged in two different layers. Therefore, such an embodiment allows for a particularly precise comparability of the detector signals.

In an embodiment, at least one of the plurality of layers is arranged between the part of the layers comprising the patterned section and the other part of the layers comprising the further patterned section. By sandwiching one or more intermediate layers between the patterned layers, a high mechanical stability can be achieved and the fluidic paths of the various patterned layers can be safely fluidically decoupled. For instance, the sandwiching layers may be reinforcement layers such as metal layers providing high robustness even against high pressure values or other harsh conditions.

In an alternative embodiment, the part of the layers comprising the patterned section is directly adjacent to the other part of the layers comprising the further patterned section. In such a scenario, a specifically compact fluidic chip device may be achieved. In other words, no intermediate layers are present in such a scenario. Fluid decoupling between the fluidic channels in the patterned section from the fluidic channels in the further patterned section may then be achieved by a lateral displacement between the various fluidic channels in the patterned section as compared to the further patterned section.

In an embodiment, the fluidic chip device comprises a processing element, particularly a flow resistor (alternatively a chromatographic column, etc.), for processing the fluid supplied at an inlet of the processing element so that the processed fluid is supplied as the further fluid at an outlet of the processing element. The differential pressure determining unit may then be configured for determining a pressure drop of the fluid as a result of the processing by the processing element. By such an embodiment, the influence of the processing element on the pressure conditions may be detected. Pressure differences may allow to derive information about the functioning of the processing element.

In an embodiment, the fluidic channels and the further fluidic channels are arranged in the corresponding layer without overlap in a projection to a plane perpendicular to a stacking direction of the layers. Looking from above onto the layer stack, i.e. looking onto an upper main surface of the uppermost layer would then, if the layers were transparent, allow to watch all fluidic channels in view of the lacking overlap between the fluidic channels and the different layers. This allows to fluidically decouple the fluidic channels in the different layers as well as to provide a stable overall structure of the layer stack.

In an embodiment, the fluidic chip device comprises a pressure source (such as a pump) for supplying the fluid to the fluidic channels under pressure and comprising a further pressure source (such as a further pump) for supplying the further fluid to the further fluidic channels under a further pressure. Therefore, even if two different pressure sources such as two different pumps supply pressurized fluids to the patterned section and the further patterned section, the pressure difference between these two pressure sources in accordance with their impact on the fluidic channels may be measured.

In an embodiment, the pressure source and the further pressure source are fluidically decoupled from one another, i.e. fluid communication therebetween may be disabled. Thus, a pressure difference between two different channels being not in interaction with one another may be measured as well.

In an embodiment, a connection between the patterned section and a rest of the layer thereof is weakened by a weakening structure, particularly a frame cut into at least one of the plurality of layers, to thereby enable a motion of the patterned section relative to the rest of the layer in response to the pressure, i.e. when a pressure is applied. Such a weakening structure may be formed by a perforation or a continuous cutting line in the layer around at least a part of the patterned section so that the patterned section can freely move relative to the rest of the corresponding layer. This allows to further increase the sensitivity of the pressure sensor, because not the entire layer, but only the patterned section has to perform the motion.

In an embodiment, the fluidic chip device further comprises a patterned reference section structurally configured as the patterned section (for instance identical thereto) but being free of a weakening structure so that the reference section remains spatially fixed in response to the pressure. A reference signal detector may be configured for detecting a reference signal of the patterned reference section in response to the pressure, and a calibration unit may be configured for calibrating the detector signal based on or using the reference signal. In such an embodiment, patterned section and patterned reference section may have the same physical structure, i.e. the same dimensions, materials, shape. The only difference between the patterned reference section and the patterned section is that the patterned reference section is spatially fixed, i.e. is not capable of vibrating relative to a remaining part of the corresponding layer. It has been recognized that also the temperature may have an effect on the signals output by the pressure detector. However, this temperature dependent part of the signal is basically the same for the patterned reference section as for the patterned section. Therefore, when a displacement of the patterned section occurs, a differential measurement between patterned reference section and patterned section allows to eliminate the temperature effects from the pressure signal of the patterned section. Therefore, the accuracy of the pressure detection may be further increased and may be rendered temperature independent.

In an embodiment, the calibration unit is configured for at least partially compensating temperature influences in the detector signal by considering the reference signal. This can be specifically performed by subtracting the reference signal from the detector signal, thereby eliminating or at least strongly suppressing the influences of temperature.

In an embodiment, the bars of the patterned section form a meander structure, a spiral structure, and/or a zig zag structure. However, any other kind of physical structures are possible as well provided that they result in an alternating sequence of fluidic channels and bars.

In an embodiment, at least a part of the layers comprises a metallic material and/or a plastic material. For example, the layers may be made of stainless steel, while polyaryletherketone (PAEK) can be another suitable material for the layers. Polyetheretherketone (PEEK) is a specific example for a plastic which might be used. The use of ceramic materials such as silicon carbide, aluminum oxide, magnesium oxide, etc. for the layers is possible as well.

In an embodiment, the pressure detector comprises a strain gauge. A strain gauge is a device used to measure the strain of an object. A usable type of strain gauge consists of a flexible backing which supports a metallic foil pattern. The gauge is attached to the object by a suitable adhesive, such as cyanoacrylate. As the object is deformed, the foil is deformed, causing its electrical resistance to change. This resistance change, which may for instance be measured using a Wheatstone bridge, is related to the strain by a certain quantity.

In an embodiment, the strain gauge is attached to the patterned section or is at least partially integrally formed with the patterned section. For example, the bars, if made of an electrically conductive material, themselves may be used as the structure of the strain gauge changing its electrical resistance upon deformation. As an alternative to such an integrally formed embodiment, the entire pressure sensor may also be provided completely separate from the patterned section.

In an embodiment, the strain gauge comprises an electric signal supply unit configured for applying an electric signal to an electrically conductive structure of the strain gauge, and a response signal analysis unit configured for analyzing a response signal received in response to the applied electric signal for generating the detector signal. Such an embodiment may make use of the effect that certain electrically conductive structures change their resistance upon deformation.

In an embodiment, the response signal analysis unit comprises a Wheatstone bridge. A Wheatstone bridge is an arrangement of resistances, of which at least a part can be changed under a certain influence, thereby allowing a very accurate measurement of pressure values in the present implementation.

In an embodiment, the pressure detector comprises an electromagnetic radiation source (such as a light source) configured for irradiating the patterned section, particularly a reflective surface of the bars, with primary electromagnetic radiation. An electromagnetic radiation detector (such as a photodiode) may be configured for detecting secondary electromagnetic radiation received from the patterned section in response to the primary electromagnetic radiation for generating the detector signal. For example, a light source may irradiate a light beam onto the patterned section which is then reflected and measured by a photodiode or another light detector. Depending on the deformation state of the patterned section, particularly the bars, it can then be determined which pressure value is present in the fluidic channels. Generally, the larger the pressure, the larger the deviation of the reflected light beam from a pressure-free condition.

In another embodiment, the pressure detector comprises a capacitive pressure detector, a resistive pressure detector, a semiconductor pressure detector, a tunneling pressure detector, and/or a position-detection based pressure detector. However, many other sensor types can be implemented. Each of these sensors are configured to be responsive to deformations of the patterned section as a result of the pressurized fluid in the fluidic channels.

In an embodiment, the patterned section is configured for being displaceable in response to the pressure in accordance with an elastic Hooke characteristic. An elastic Hooke characteristic may denote a characteristic in which a back driving force is proportional to the elongation of the patterned section.

In an embodiment, two of the layers each comprise a patterned section, wherein the two layers are buried within a stack of the plurality of laminated layers (i.e. are not surface layers) and are arranged symmetrically to one another (and with respect to a central layer) within the stack. By such a symmetric arrangement of the layers having patterned sections the deformations in response to a pressurized fluid will generate forces on the laminated layer stack which may at least partially compensate each other so that the entire load acting on the fluidic chip device can be reduced.

In an embodiment, the patterned section comprises a first sub-section and a second sub-section, wherein the fluidic channels of the first sub-section are arranged with a parallel offset relative to the fluidic channels of the second sub-section to be symmetrically arranged with respect to a neutral axis. Hence, in a cross-sectional view, the patterned section may have a step-like shape. The neutral axis is the axis on which no forces are acting. Therefore, with such two horizontal sub-sections connected by a vertical connection line defining the value of the offset an S-shaped deformation characteristic may be achieved.

In an embodiment, the patterned section is configured as a spring bellows. Therefore, the patterned section behaves like a spring upon applying a force by the pressurized fluid.

In an embodiment, the fluidic chip device comprises a diagnosis unit configured for diagnosing, based on the detector signal, a functional capability of the fluidic chip device. For instance, a look-up table may store values indicative of a proper functioning which can be determined experimentally. Upon measuring actual pressure values or similar parameters, the diagnosis unit may compare such data and may output information indicative of a proper functioning or not.

In an embodiment, the diagnosis unit is configured for performing the diagnosing based on at least two detector signals relating to at least two different positions within the fluidic chip device. Measuring at different positions within the layer stack may allow to broaden the data basis so as to obtain a better independency of artifacts based on local effects.

In an embodiment, the fluidic chip device comprises at least one fluidic interface, particularly at least one fluid inlet port for supplying a fluid to at least one of the plurality of layers and at least one fluid outlet port for draining a fluid received from at least one of the plurality of layers, for supplying or draining a fluid and being in fluid communication with at least a part of the plurality of layers. Therefore, several fluid ports for introducing and receiving fluid may be foreseen.

In an embodiment, the fluidic chip device comprises at least one electric interface, particularly at least one electric signal inlet port for supplying an electric signal to at least one of the plurality of layers and at least one electric signal outlet port for transmitting an electric signal received from at least one of the plurality of layers, for conducting an electric signal and being in electric communication with at least a part of the plurality of layers. Apart from the fluidic interfaces, the fluid chip device may also have electric interfaces allowing for signal transport.

In an embodiment, at least one of the layers has a thickness in a range between about 25 µm and about 300 µm, particularly in a range between about 50 µm and about 200 µm, more particularly in a range between about 70 µm and about 120 µm. The extension of the layers in the other directions may be significantly larger as compared to the signals, for instance may be in a range between 1 mm and 10 cm, particularly 1 cm to 5 cm. Therefore, the individual layers may be flat layers or sheets.

In an embodiment, the fluidic chip device comprises a processing element arranged in the fluidic conduit and configured for interacting with the fluidic sample. Such a processing element may be a chromatographic column, integrated in the layer stack. Other processing elements are possible as well. For example, a flow resistor may be the processing element.

At least a part of a processing element provided in the substrate may be filled with a fluid separating material. Such a fluid separating material which may also be denoted as a stationary phase may be any material which allows an adjustable degree of interaction with a sample so as to be capable of separating different components of such a sample. The fluid separating material may be a liquid chromatography column filling material or packing material comprising at least one of the group consisting of polystyrene, zeolite, polyvinylalcohol, polytetrafluorethylene, glass, polymeric powder, silicon dioxide, and silica gel. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 µm to essentially 50 µm. Thus, these beads may be small particles which may be filled inside the separation column. The beads may have pores having a size in the range of essentially 0.008 µm to essentially 0.03 µm. The fluidic sample may be passed through the pores, wherein an interaction may occur between the fluidic sample and the pores. By such effects, separation of the fluid may occur.

The fluidic chip device may be configured as a fluid separation system for separating components of the mobile phase. When a mobile phase including a fluidic sample is pumped through the fluidic chip device, for instance with a high pressure, the interaction between a filling of the column and the fluidic sample may allow for separating different components of the sample, as performed in a liquid chromatography device or in a gel electrophoresis device.

However, the fluidic chip device may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic chip device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic chip device may be or may be implemented in different technical environments, like a detector device, a test device for testing a device under test or a substance, a device for chemical, biological and/or pharmaceutical analysis, a capillary electrophoresis device, a liquid chromatography device, a gas chromatography device, an electronic measurement device, or a mass spectroscopy device. Particularly, the fluidic chip device may be a High Performance Liquid device (HPLC) device by which different fractions of an analyte may be separated, examined and analyzed.

The fluidic chip device may be configured to conduct a liquid mobile phase through the processing element and optionally a further processing element. As an alternative to a liquid mobile phase, a gaseous mobile phase or a mobile phase including solid particles may be processed using the fluidic chip device. Also materials being mixtures of different phases (solid, liquid, gaseous) may be analyzed using exemplary embodiments.

The fluidic chip device may be configured to conduct the mobile phase through the processing element(s) with a high pressure, particularly of at least 600 bar, more particularly of at least 1200 bar. In the context of such a high pressure application, the corset function of the interconnected reinforcing arrangement may be particularly of interest.

The fluidic chip device may be configured as a microfluidic chip device. The term "microfluidic chip device" may particularly denote a fluidic chip device as described herein which allows to convey fluid through microchannels having a dimension in the order of magnitude of micrometers (μm) or less.

The fluidic chip device may be configured as a nanofluidic chip device. The term "nanofluidic chip device" may particularly denote a fluidic chip device as described herein which allows to convey fluid through microchannels having a dimension in the order of magnitude of nanometers (nm) or less.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

Figure 1:
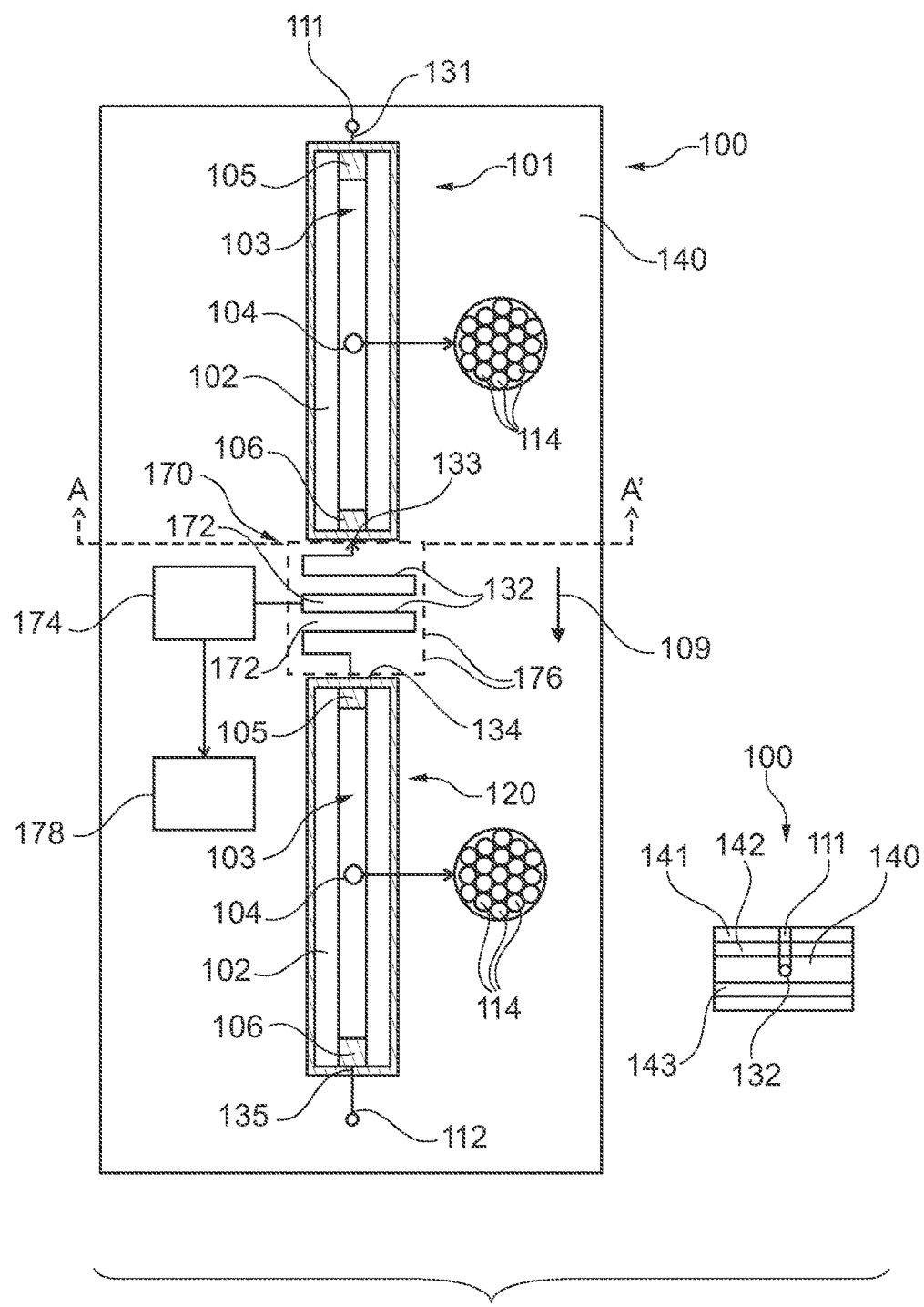
FIG. 1 shows one layer located in a center of a layer stack of a fluidic device according to an exemplary embodiment of the invention.

The illustration in the drawing is schematic.

Figure 17:
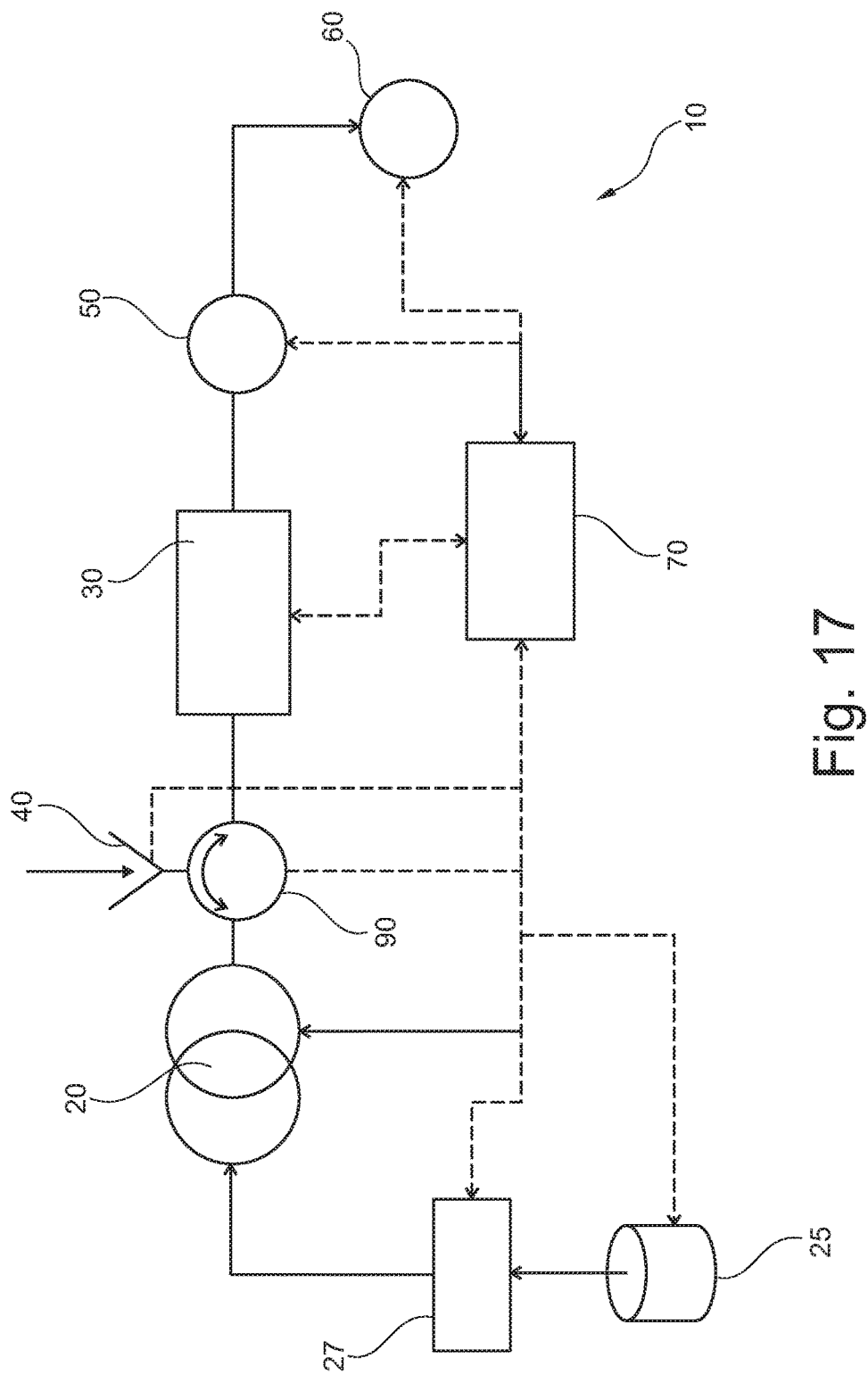
FIG. 17 shows a liquid chromatography system part of which may be realized by a fluidic chip device according to an exemplary embodiment of the invention.

Referring now in greater detail to the drawings, FIG. 17 depicts a general schematic of a liquid separation system 10. A pump 20 receives a mobile phase from a solvent supply 25, typically via a degasser 27, which degasses and thus reduces the amount of dissolved gases in the mobile phase. The pump 20—as a mobile phase drive—drives the mobile phase through a separating device 30 (such as a chromatographic column) comprising a stationary phase. A sampling unit 40 (having a needle/seat arrangement depicted in FIG. 17 schematically) is provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). A switchable valve 90 can be operated so as to adjust a desired fluidic coupling within the liquid separation system 10. The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

A switchable valve 90 can be operated so as to adjust a desired fluidic coupling within the liquid separation system 10.

In the following, multiple embodiments of the invention related to pressure detection in fluidic chip devices will be explained. Such fluidic chip devices may include any combination of one or more of the components shown in FIG. 17.

In the following, referring to FIG. 1, a fluidic chip device 100 according to an exemplary embodiment will be explained.

The larger image in FIG. 1 shows a functional, processed polyimide core layer 140 of a multi-layer stack of the fluidic chip device 100. The smaller image in FIG. 1 shows a cross-sectional side view of the entire multi-layer stack of the fluidic chip device 100, taken along line A-A' of the larger view, showing the core layer 140 embedded between other layers, as will be described below in further detail. In the larger image of FIG. 1, layers 141 and 142 (shown in the smaller image) are not shown, so as to provide a top view of the core layer 140.

The fluidic chip device 100 is adapted as a system for carrying out liquid chromatography investigations. The fluidic chip device 100 for separating different components of a fluid or a mobile phase which can be pumped through the apparatus 100 comprises a pre-column 101 for pre-processing (for instance sample preparation or sample enrichment) the fluidic sample and comprises an analytical or main column 120 for post-processing the fluidic sample which has already passed the pre-column 101. In other words, the system 100 is a two-stage fluid separation system. Other embodiments may include only a one-stage fluid separation system having only one column, or a multi-stage fluid separation system or a workflow integration system having multiple (for instance three, four or more) columns. Workflows imply the processes previous to the separation as: column enrichments, digestions, etc.

In the embodiment of FIG. 1, each of the fluid separating columns 101, 120 comprises a column tube 102 which is shaped to define closed packed channels, for instance having a rectangular cross-section. Within each of these fluid separating columns 101, 120, a tubular reception 103 is defined which is filled with a package composition 104.

The fluidic chip device 100 is adapted as a liquid chromatography device and has, in each of the columns 101, 120, a first frit 105 close to an inlet 131, 134 of the respective columns 101, 120, and a second frit 106 provided at an outlet 133, 135 of the respective column 101, 120. The first frit 105 forms the inlet of the respective column 101, 120 and is provided upstream the respective column tube 102. The second frit 106 forms the outlet of the respective column 101, 120 and is located downstream of the respective column tube 102. A flowing direction of the fluid which is separated using the fluidic chip device 100 is denoted with the reference numeral 109.

A fluid pump (not shown) is provided externally from the chip 100 and pumps fluid under pressure of, for instance, 1000 bar through a connection tube or fluidic conduit 111 (extending perpendicular to the paper plane of FIG. 1) and from there to the inlet 131 of the pre-column 101, through the first frit 105 into the column tube 102. After having left the column tube 102, that is to say after having passed the second frit 106, a meandric intermediate tube 132 connected to an outlet 133 of the pre-column 101 transports the pre-processed analyte to the inlet 134 of the main column 120. The internal construction of the main column 120 is similar to that of the pre-column 101, but may (or may not) differ from the pre-column 101 with respect to size and fluid separating material 114 filled in the tubular reception 103.

In a further stage, the sample is further separated in the main column 120, and the further separated sample leaves the outlet 135 of the main column 120. After having left the column tube 102 of the main column 120, that is to say after having passed the second frit 106 of the main column 120, a second fluidic conduit 112 (extending perpendicular to the paper plane of FIG. 1) transports the separated analyte to a container and analysis unit (not shown) positioned outside of the chip 100.

The column tubes 102 comprises the filling 104. In other words, a packing composition 104 comprising a plurality of silica gel beads 114 is inserted into the hollow bore 103 of the column tube 102 of each of the columns 101, 120.

The mobile phase is first conducted through the pre-column 101. By selecting an appropriate ACN concentration in a $H_2O$ environment, a fraction of the fluidic sample may first be trapped at a particular position within the column tube 102 of the pre-column 101. This procedure may be denoted as a pre-focusing or pre-separation. Components of the mobile phase which are not trapped in the pre-column 101 are collected in a waste unit (not shown).

Afterwards, the $ACN/H_2O$ concentration ratio within the column tube 102 of the pre-column 101 may be selectively modified so as to elute the sample trapped in the column tube 102 of the pre-column 101. Then, the fluidic sample will move through the outlet 133 of the pre-column 101, and will enter the inlet 134 of the main column 120 to be trapped in a portion close to the outlet of the frit 105 of the main column 120.

When the fluid passes through the main column 120, components which differ from a fraction to be separated may simply pass through the column 120 without being trapped and may be collected in a waste (not shown). At the end of this procedure, a band of the fraction of the fluidic sample of interest is trapped at a particular position within the main column 120. By again modifying the concentration ratio $ACN/H_2O$, for instance by gradually modifying the respective contributions of these two components, the trapped sample may be released from the main column 120 and may be conducted to another fluidic member for further processing.

Layer 140 in FIG. 1 is so to say the active layer of the layer stack, in which a plurality of the fluid separation procedures are carried out. However, the side view of the layer stack 100 shown in FIG. 1 as well illustrates that two outer boundary layers 141, 143 form the outer layers of the layer stack and are made from a plastic material such as polyimide. Sandwiched between the active layer 140 and one of the outer boundary layers 141 is a reinforcing metal layer 142, for instance made of stainless steel. Each of the layers 140 to 143 is laminated on both of its opposing main surfaces (the large view of FIG. 1 shows one main surface of the active layer 140) with main surfaces of adjacent layers over the entire area of the main surfaces (outer boundary layers 141 and 143 are the only ones in which only one of the two main surfaces are laminated, the other one is exposed) by applying glue or adhesive and connecting them by applying some pressure. As a result of this lamination process, it is possible to obtain a very robust layer stack, which is capable of withstanding pressure values of 600 bar, 1200 bar or even more. High pressure values may be present in the channels 111, 132, 112 during a HPLC analysis. The layers 141, 142 and 140 comprise recesses or holes or channels, which together form the fluidic conduit 111 (layers 141, 142 and 140, see FIG. 1), the fluidic conduit 132 (only layer 140) and the fluidic conduit 112 (again in layers 141, 142, 140). Therefore, these recesses or holes or channels may be in alignment to one another, so as to form together a fluidic path of the fluidic chip device 100.

As can be taken from FIG. 1, layer 140 comprises a patterned section 170 of an alternating sequence of bars 172 and fluidic channels 132 for conducting the fluid under pressure. The patterned section 170 is configured for being displaceable in response to the pressure. Furthermore, a pressure detector 174 is configured for responding to the displacement of the patterned section by generating a detector signal being indicative of a value of the pressure. A connection (e.g., a weakening structure 176) between the patterned section 170 and a rest of the layer 140 is selectively weakened by a perforation or complete cutting line which is provided in a frame-like way in FIG. 1. Thus, the patterned section 170 is cut out from the rest of the layer 140 to thereby enable a motion of the patterned section 170 relative to the rest in response to the pressure. In other words, the metal layer 140 is patterned in the section 170 so as to form the fluidic channels 132 separated by the remaining bars 172 of metal material of the layer 140. When the fluid flows through the channel 132 with high pressure, this will cause a deformation of the mechanically weakened and freely movable patterned structure 170 so that the pressure sensor 174 can detect this motion or elongation. This detection signal is indicative for the pressure of the fluid in the fluidic channels 132. In FIG. 1, the channels 132 together form a meander structure. When the pressure signal has been detected by the pressure detector 174, the result may be supplied in the form of an electronic signal to diagnosis unit 178 which is configured for diagnosing, based on the detector signal, a functional capability of the fluidic chip device 100. Hence, the diagnosis unit 178 may detect whether a generated pressure signal is acceptable, for instance is within a range which is considered to be appropriate for the fluidic chip device 100.

Although FIG. 1 shows that components 174, 178 are part of the multi-layer structure, i.e. are integrated therein, they can also be at least partially be provided apart or separate from the layer stack. For the pressure detector 174, it may be preferred if it is arranged within the layer stack to obtain a high accuracy of the detection. Signal evaluation is performed by diagnosis unit 178, for instance a microprocessor or a central processing unit (CPU), which can however also be performed outside of the layer stack.

It should be said that active layer 140 is located asymmetrically in the layer stack of FIG. 1, i.e. that the distance of active layer 140 from an upper surface and from a lower surface of the layer stack is different. By taking this measure, it can be ensured that the sensor detection can be performed with high precision, since the pressurized fluidic channels 132 are then located at a distance from the neutral axis of the layer stack. Without wishing to be bound to a specific theory, it is presently believed that fluidic channels 132 spaced significantly from the neutral axis experience a stronger displacement under pressure as compared to fluidic channels 132 being located very close to the neutral axis.

Figure 2:
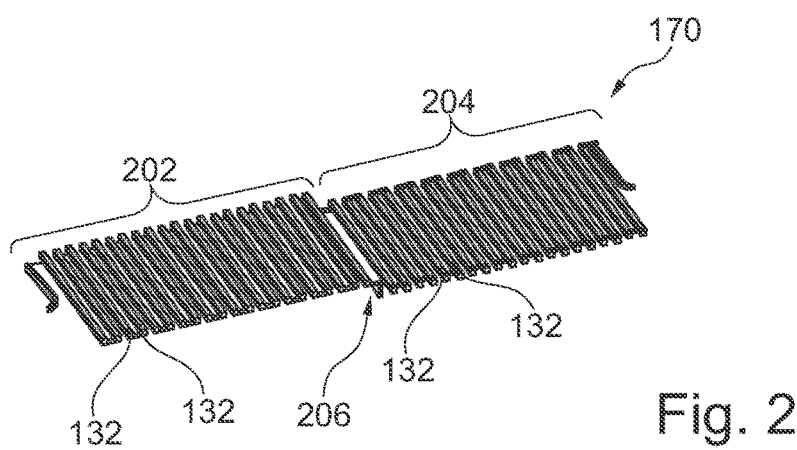
FIG. 2 shows a patterned section of a fluidic chip device according to an exemplary embodiment of the invention, wherein the patterned section has two sub-sections arranged with a vertical offset relative to one another.

FIG. 2 shows a detailed view of an embodiment of a patterned section 170. In this embodiment, the patterned section 170 comprises a first sub-section 202 and a second sub-section 204 which are arranged in two different planes which are parallel to one another. The fluidic channels 132 (as well as the bars) of the first sub-section 202 are therefore arranged with a parallel offset 206, i.e. a vertical shift, relative to the fluid channels 132 (as well as the bars) of the second sub-section 204 so as to be symmetrically arranged with respect to a neutral axis. Thus, a pressure sensor arrangement based on planar metallic structures is provided. FIG. 2 shows a corresponding channel structure in a multi-layer fluidic chip device. For instance, thin metal foils of a thickness of for instance 0.02 mm to 0.5 mm are provided and are patterned. Such a structure forms a spring bellows which deforms proportionally to the applied pressure, i.e. elastically.

Figure 3:
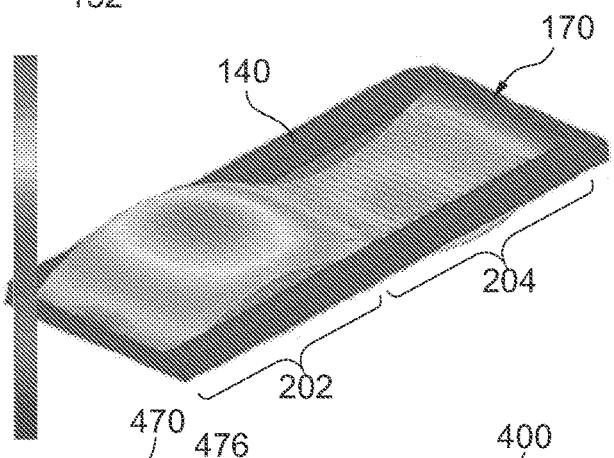
FIG. 3 shows an S-shaped elongation characteristic of the patterned section of FIG. 2 in the presence of a fluid flowing under high pressure through the conduits between the bars of the patterned section.

FIG. 3 shows again the patterned section 170 of FIG. 2 and shows an S-shaped deformation. An S-shaped deformation is appropriate for a high signal amplitude, since this allows to constitute at the same time tension stress and compressive stress. The image of FIG. 3 has been obtained by a finite element analysis for a pressurized layer arrangement.

Figure 4:
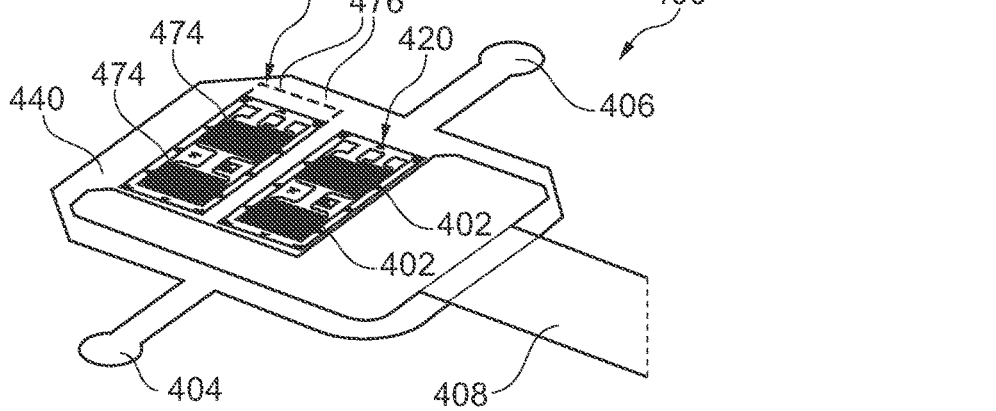
FIG. 4 shows a three-dimensional view of a fluidic chip device according to an exemplary embodiment of the invention including a data processing part.
Figure 4:
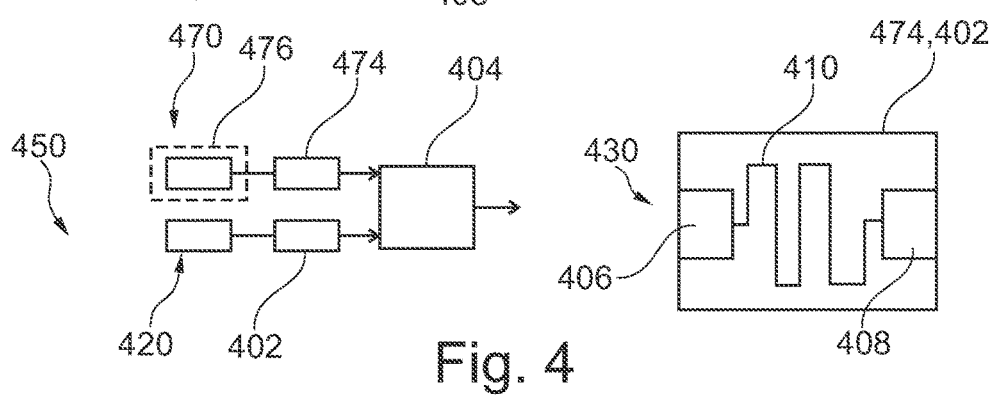

FIG. 4 shows a fluidic chip device 400 according to an exemplary embodiment of the invention.

More precisely, the illustration of FIG. 4 only shows a portion of such a fluidic chip device 400, wherein other layers above and below a layer of interest 440 are not shown in FIG. 4. The embodiment of FIG. 4 shows that, within the layer 440, not only a patterned section 470 with a surrounding weakening structure 476, but additionally a patterned reference section 420 is provided which is shaped and dimensioned in the same way as the patterned section 470 but being free of the weakening structure 476. In other words, the reference section 420 is arranged to remain spatially fixed in response to applied pressure flowing through fluidic channels between bars of the patterned reference section 420. The reason for this is that the further patterned section 420 is not structurally separated from the rest of the layer 440 so that it cannot follow or basically not follow any pressure induced motion.

FIG. 4 furthermore shows that a strain gauge is attached to the top of the patterned section 470, as a pressure detector 474. Additionally, a reference signal detector 402 in the form of another strain gauge (having the same structure as the strain gauge of the pressure detector 474) is provided. The patterned section 470 and the further patterned section 420 are constructed as similar as possible.

As shown in a first detailed view 450 in FIG. 4, a calibration unit 404 is provided which is configured for calibrating the detector signal generated by the detector 474 using the reference signal generated by the further detector 402. Particularly, the calibration unit 404 may subtract the signal of the patterned reference section 420 from the signal of the patterned section 470 so as to eliminate any temperature induced effects on the detector signal. In other words, by subtracting a baseline signal (coming from the further patterned section 420) from the signal related to the patterned section 470, any temperature-based artifacts (and other artifacts which do not relate to the deformation of the fluidic channels resulting from the fluid pressure) can be eliminated or at least suppressed.

A second detailed view 430 of FIG. 4 shows the signal paths involved in the detection using the strain gauges of the detector 474 and the further detector 402. An electric signal supply unit 406 is provided and configured for applying an electric signal to an electrically conductive structure 410, a meander in the present embodiment, of the strain gauge forming the pressure detector 474 or 402, respectively. A response signal analysis unit 408 is further provided which is configuring for analyzing a response signal received in response to the applied electric signal for generating the detector signal. Such signals may be supplied by a flex board or pad 408 providing for an electric contacting of the fluidic chip device 400. For a precise detection of the pressure signals by the strain gauges forming the pressure detector 474 and the further pressure detector 402, respectively, Wheatstone bridges may be provided as part of the detectors 474, 402, respectively.

Hence, FIG. 4 shows an arrangement of strain gauges for determining the applied pressure with a temperature compensation reference structure on the metal structure of the patterned layer 440. Therefore, with the implementation of an appropriate detection system (in the shown embodiment strain gauges), the degree of deformation can be estimated which can be transferred, via a suitable signal transformation, into an electrical output signal. Advantages of the arrangement of FIG. 4 are that it can be simply integrated with other fluidic components without an additional effort for connection elements. The system further has a very small dead volume of the sensor unit, it is hermetically sealed, and there are many design parameters for forming the internal channel structure (deformation body) in accordance with certain requirements of a certain application.

Figure 5:
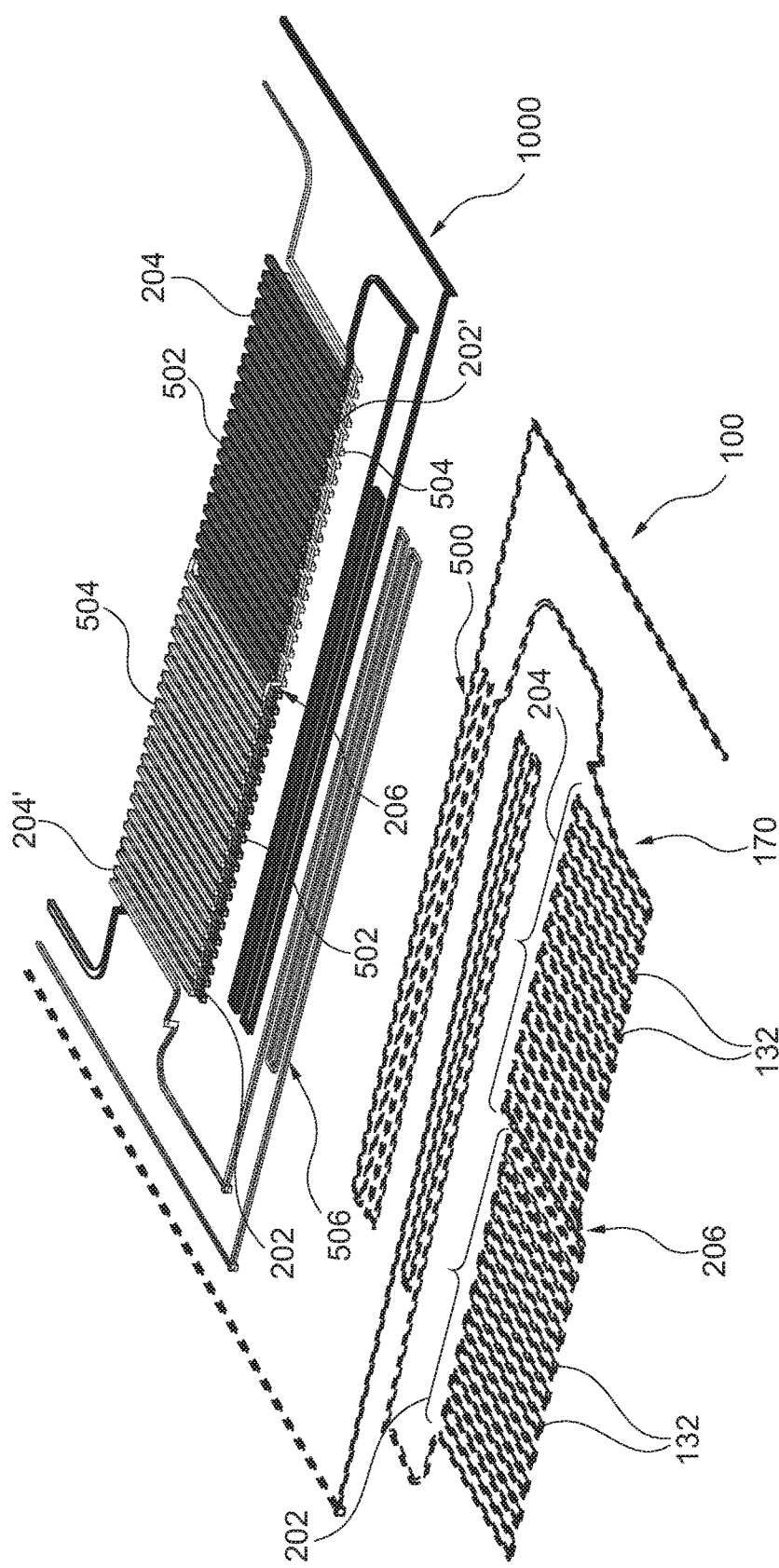
FIG. 5 shows a perspective view of fluidic channels of patterned metal layers for a differential pressure sensor and for an absolute pressure sensor according to exemplary embodiments of the invention.

FIG. 5 is a perspective view of a part of the fluidic chip device 100 for an absolute pressure measurement, and also shows a differential pressure measurement structure 1000 which will be described in further detail referring to FIG. 10. The fluidic chip device 100 is only shown with regard to the channels 132 of the patterned metal layers (bars are not shown).

Additionally, a temperature compensation structure 500 (which can be similar to the reference patterned section 400) is shown in FIG. 5 as well.

Moreover, FIG. 5 shows, for the differential pressure arrangement, fluidic chip device 1000 which is basically composed of two interleaved patterned sections 502, 504. A first interleaved patterned section 502 is constituted with the two sections 202, 204 as shown for the absolute pressure sensor 100. A second patterned section 504 has an inverse structure, so that a sub-section 204' is shown on the left-hand side and a sub-section 202' is shown on the right-hand side for the further patterned section 504. At the position of the offset 206 there is an intersection of the sub-sections 202, 204 of the patterned section 502 and of the sub-sections 204', 202' of the further patterned section 504. Additionally, a temperature compensation structure 506 is provided also for the differential pressure measurement fluidic chip device 1000.

Figure 6:
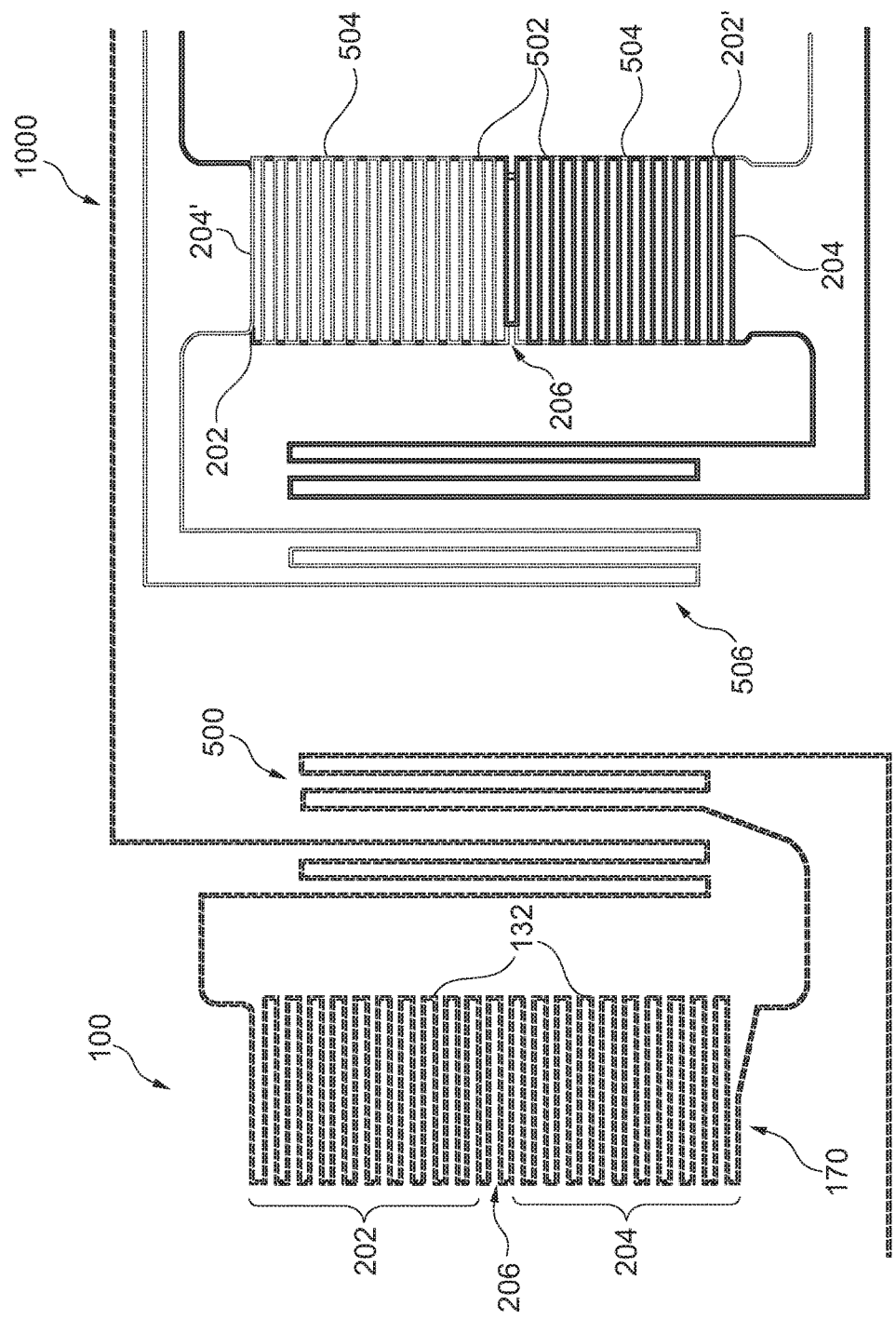
FIG. 6 shows a plan view of the structure of FIG. 5.

FIG. 6 is a plan view of the three-dimensional structure of FIG. 5.

Figure 7:
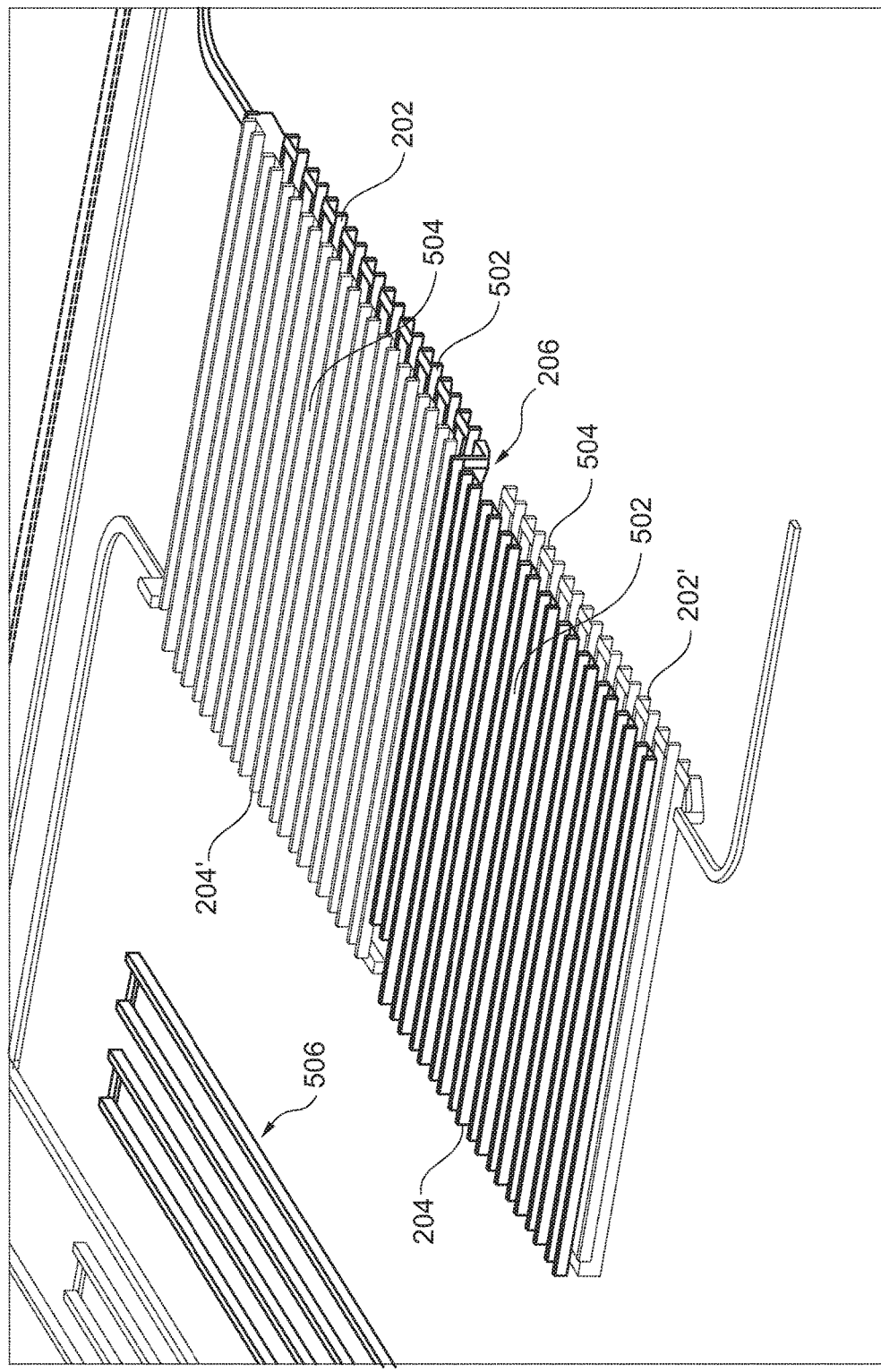
FIG. 7 shows a detailed view of the differential pressure sensor of FIG. 5.

FIG. 7 is a detailed view of FIG. 5 and only shows the portion relating to the differential pressure measurement, i.e. fluidic chip device 1000.

Figure 8:
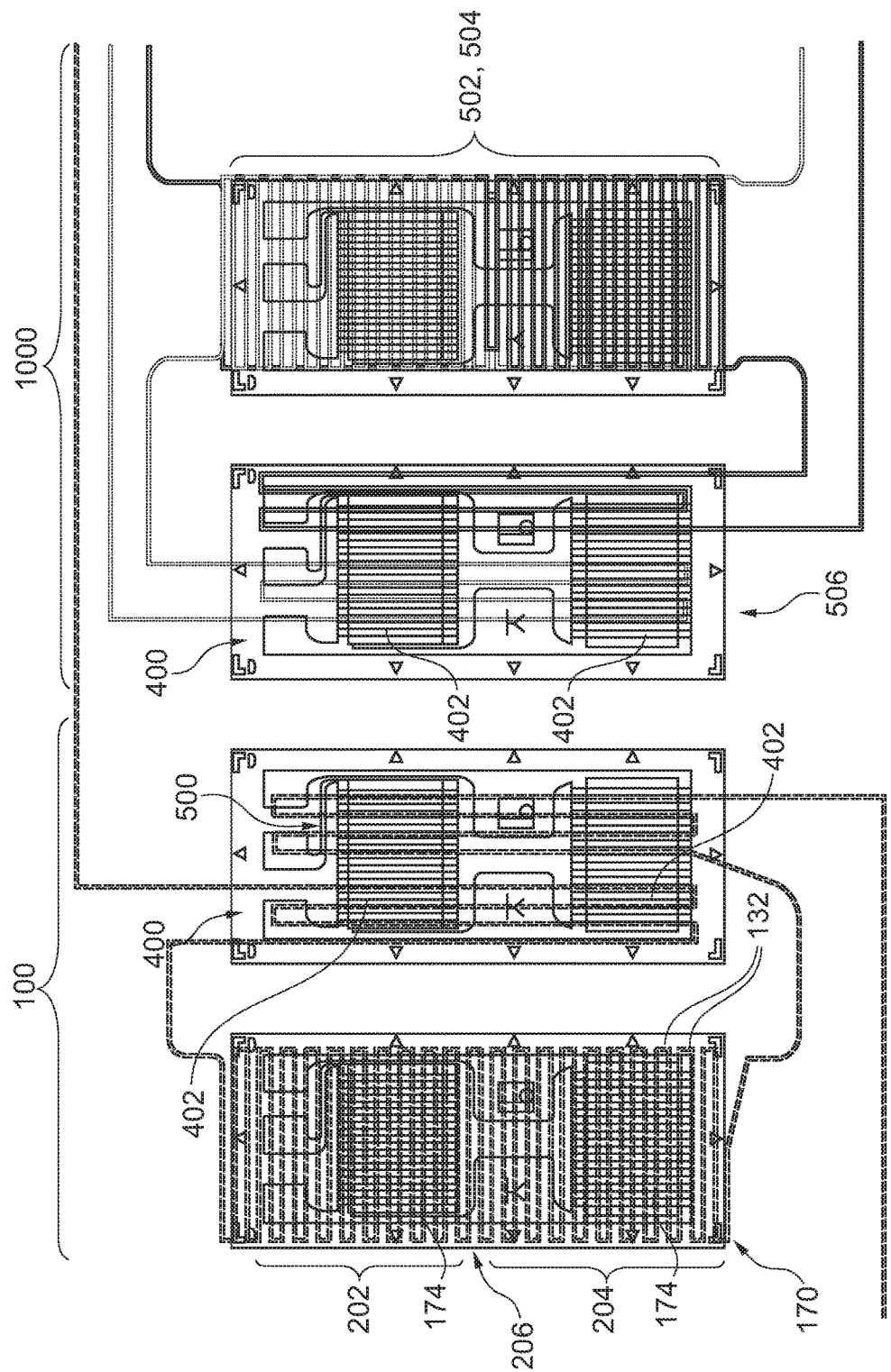
FIG. 8 shows an arrangement of strain gauge detectors with half bridges above channels and bars of a fluidic chip device according to an exemplary embodiment of the invention.

FIG. 8 is a view which relates to FIG. 6 but has overlaid the arrangement of strain gauges as detectors 174, 402, as has been explained referring to FIG. 4.

Figure 9:
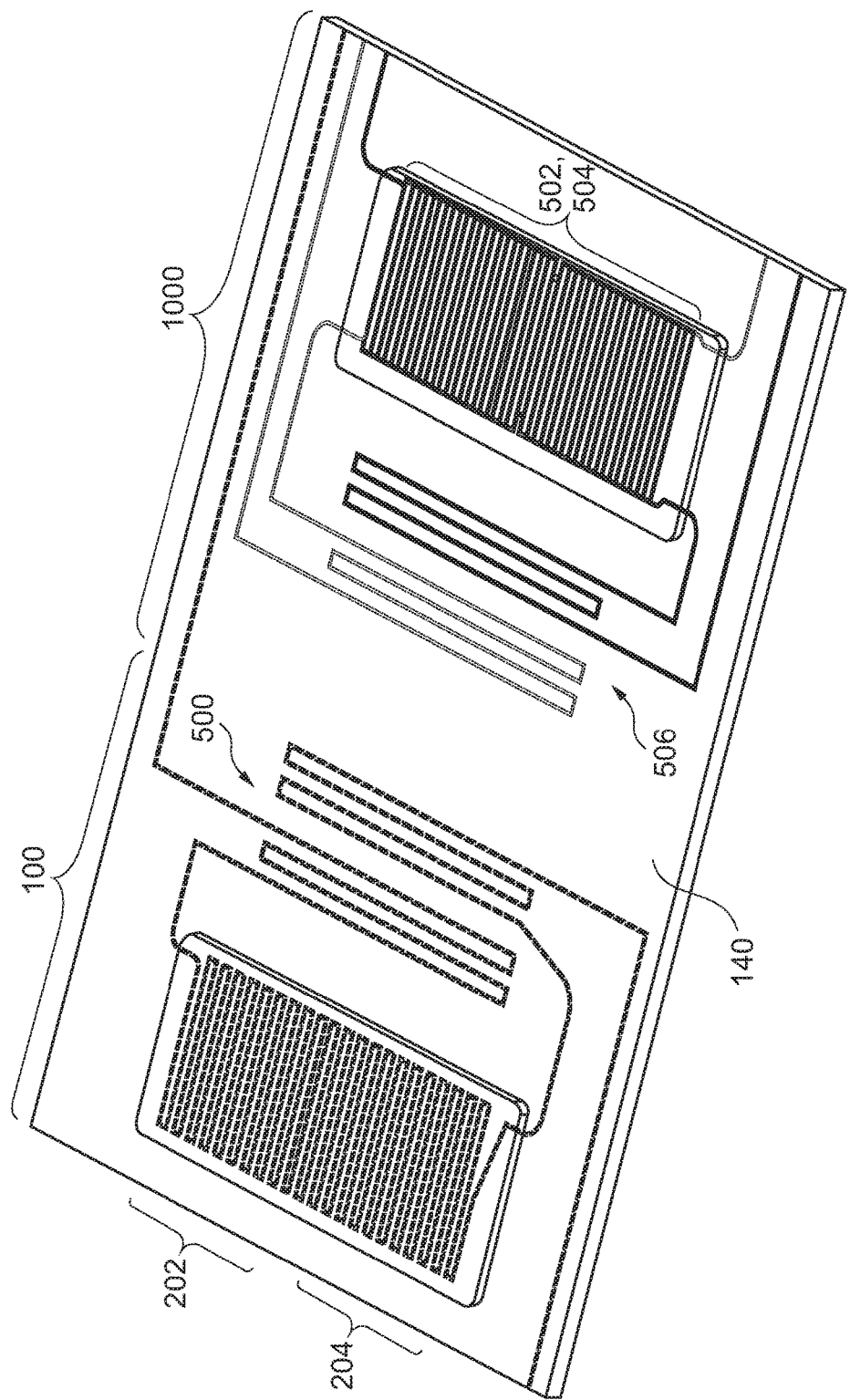
FIG. 9 shows, on the left-hand side, an absolute pressure sensor and on the right-hand side a differential pressure sensor according to exemplary embodiments of the invention.

FIG. 9 is a symmetric view of the two sensors 100, 1000 on a single layer 140. On the right-hand side, the differential sensor 1000 is shown with the opportunity of a deformation by exertion of pressure with an S-shaped elongation. On the very right-hand side the strain gauge beam arrangement is shown with the opportunity to deform in an S-shaped way.

In the following, referring to FIG. 10, a fluidic chip device 1000 with the differential pressure measurement characteristic will be explained in more detail.

In certain applications (e.g. in HPLC instrumentation) it is necessary or advantageous to provide differential pressure measurement, especially measurement of comparably small difference between two high pressure values in fluids, such as but not limited to e.g. measurement of pressure drop at a flow restrictor built into a high pressure path, so that both measurement zones (restrictor ends) are subject to high pressure with only a slight difference between the high pressure values. Measurements by means of multiple separate pressure sensors are not always practicable due to additional disturbances or errors originating from separate electronic pathways, temperature differences between sensors, etc.

Therefore it can be advantageous to combine two pressure sensing structures of the kind described above to a differential pressure sensor. Especially advantageous can be an integration of the sensor structures into a microfluidic device, e.g. a planar structure of the art or similar to that described above with the difference, that two planes or layers comprising fluidic channels connected to different pressure sources are placed one over another, preferably the channels in the planes being shifted in respect to each other as shown in the figures, such as their projections do not overlap.

The channels may be interconnected to a first pressure inlet and can be connected to a first pressure source; the further channels are interconnected to a second pressure inlet and can be connected to a second pressure source.

Applying equal pressure to both pressure inlets would not result in a total deformation of the pressure sensor because the strains on both sides of the sensor would counterbalance each other. On the contrary, difference between the both pressures would result in a deformation of the sensor structure, which can be assessed by electronic means (strain gauge, capacitive, optical, inductive, semiconductor, tunneling etc. deformation or position sensors).

Figure 10:
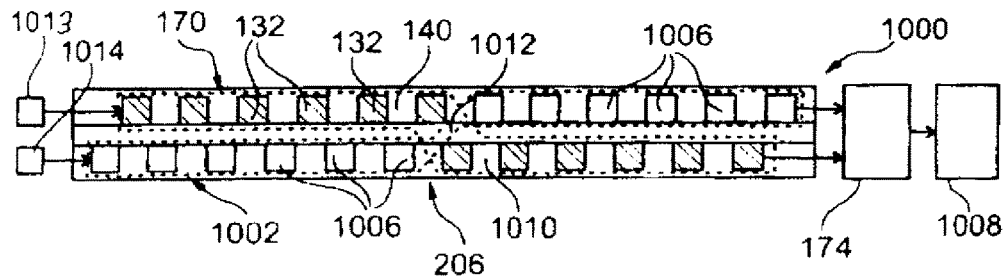
FIG. 10 shows a cross-sectional view of a multi-layer structure having a differential pressure detector according to an exemplary embodiment of the invention in an operation mode without deformation.

Coming now to FIG. 10, FIG. 10 shows a cross-sectional view through the layer sequence, wherein the above-mentioned layer 140 and additional layers 1012, 1010 are shown. However, this principle can be applied to any desired number of layers. The cross-sectional view of FIG. 10 shows the patterned section 170 with the fluidic channels 132 being drawn as hashed squares. It can be taken from FIG. 10 that these fluidic channels 132 are arranged in two different layers, i.e. layer 140 on the left-hand side of FIG. 10 and layer 1010 on the right-hand side of FIG. 10. Additionally, a further patterned section 1002 of an alternating sequence of further fluidic channels 1006 and further bars (material between adjacent further fluidic channels 1006) is provided. The left-hand side part of the further fluidic channels 1006 is arranged in the layer 1010, whereas the right-hand side part of the fluidic channels 1006 is arranged in layer 140. Therefore, as also shown in FIG. 5 to FIG. 9, a vertical offset 206 is present for both the patterned section 170 and the further patterned section 1002.

A first fluid can be conducted through the channels 132 of the first patterned section 170 powered or pressurized by a first pump 1013. A second pump 1014 separately pumps another fluid through the channels 1006 of the further patterned section 1002. Hence, the pressure detector 174 which is only shown schematically in FIG. 10 but can also be realized as one or more strain gauges, is also configured for responding to the displacement of the further patterned section 1002 by generating a further detector signal being indicative of a value of the pressure of the further fluid. Therefore, the two detector signals supplied to the pressure detector 174 are, individually, indicative of the pressure value of the fluid in the channels 132 and of the fluid in the channels 1006, respectively. However, absolute pressure measurement is also related with a certain inaccuracy. By however performing a differential analysis of the detector signal and the further detector signal in a differential pressure determining unit 1008 coupled to an output of the pressure detector 174, it is possible to determine information relating to a pressure difference between the fluid and the further fluid based on the detector signal and based on the further detector signal. In other words, the differential pressure determining unit 1008 outputs the signal which is indicative of the pressure difference between the fluids flowing in channels 132, 1006.

In the shown embodiment, the further patterned section 1002 is assigned to the same two layers 140, 1010 as the patterned section 170. However, this can be more than two layers or even the same layer. The accuracy of the pressure detection is high, if the same layers are used for the different patterned sections 170, 1002.

Figure 11:
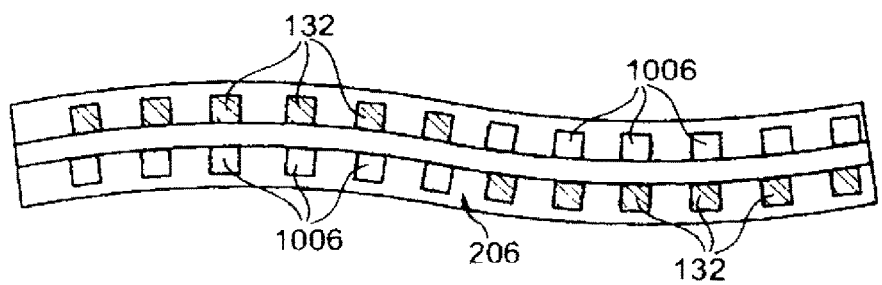
FIG. 11 shows the arrangement of FIG. 10 in the presence of a deformation caused by fluidic pressure.

FIG. 11 is an illustration showing only a part of the components of FIG. 10 but relating to the same structure. It can be taken from FIG. 11 that the application of a pressurized fluid to the channels 132 and to the channels 1006, respectively, results in an S-shaped deformation of the respective layer stack. This deformation results in the detector signal and the further detector signal which can be evaluated by the pressure detector 174 and the differential pressure analysis unit 1008.

Figure 12:
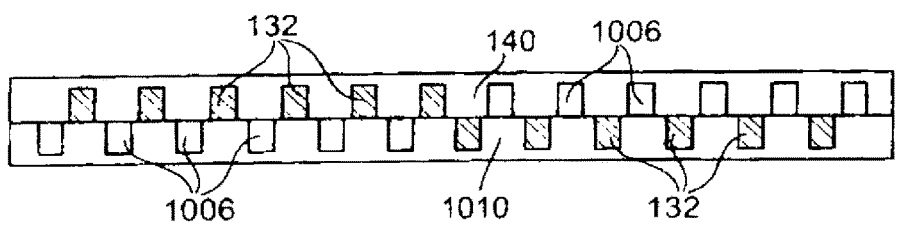
FIG. 12 shows a cross-sectional view of a fluidic chip device according to another exemplary embodiment in accordance with differential pressure measurement and patterned sections in directly adjacent layers.

FIG. 12 shows an alternative embodiment in which no intermediate layer 1012 is present between the layers 140, 1010. Hence, FIG. 12 shows an alternative layout of the channels in the sensor structure, not requiring an intermediate layer.

Figure 13:
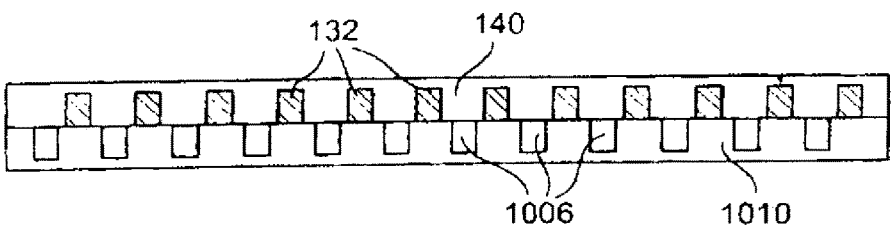
FIG. 13 is yet another exemplary embodiment of a fluidic chip device with differential pressure measurements according to an exemplary embodiment of the invention with patterned sections is entirely different layers.

FIG. 13 shows an embodiment in which the channels 132 are all formed only in one layer 140, whereas all channels 1006 are formed in another layer 1010. Placement of the sensor channels of either pressure inlet on only one side of the structure respectively as shown in FIG. 13 is hence also possible, which would however result in arc rather than S-shape deformation of the measurement structure.

Figure 14:
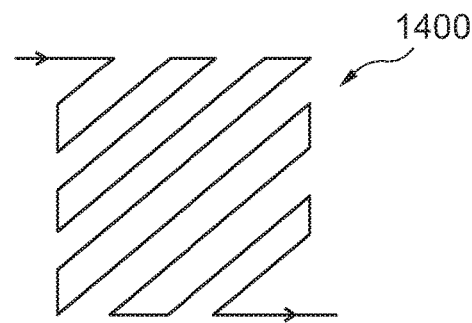
FIG. 14 shows a zig zag structure of a patterned section of a fluidic chip device according to an exemplary embodiment of the invention.

FIG. 14 shows that the patterned section does not necessarily have to have channels in a meander-shaped way, but that a zig zag structure 1400 is possible as well.

Figure 15:
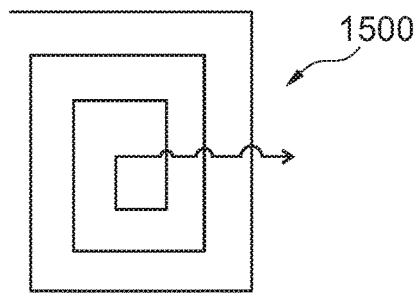
FIG. 15 shows a spiral structure of a patterned section of a fluidic chip device according to an exemplary embodiment of the invention.

FIG. 15 shows that also a spiral structure 1500 is possible.

Figure 16:
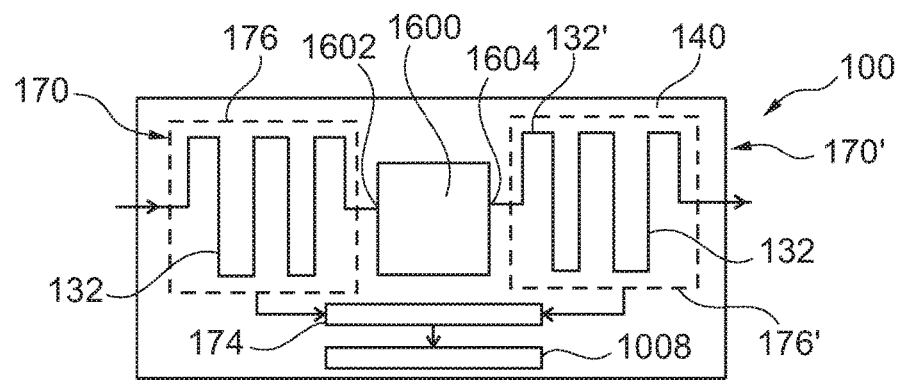
FIG. 16 is a plan view of a fluidic chip device according to an exemplary embodiment of the invention.

FIG. 16 shows that the fluidic chip device 100 can have a processing element 1600 such as a flow restrictor or a chromatographic column. A fluid is supplied via the channels 132 of a first patterned section 170 towards an inlet 1602 of the processing element 1600. After the fluidic processing, the fluid exits the processing unit 1600 via a fluid outlet 1604 and supplies the fluid to channels 132' of another patterned section 170'. The patterned section 170' also has a weakening structure 176' and can therefore follow a fluid pressure by a certain deformation. If the signals from both patterned sections 170, 170' are supplied to the pressure detector 174, a pressure drop at the processing element 1600 can be measured. A diagnosis unit 1008 can then determine whether the pressure drop is appropriate, i.e. whether the processing unit 1600 functions correctly.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A fluidic chip device configured for processing a fluid, the fluidic chip device comprising:
    a plurality of layers laminated to one another;
    wherein at least a part of the layers comprises a patterned section of an alternating sequence of bars and fluidic channels for conducting the fluid under pressure along a resultant flow direction, the patterned section having a length along the resultant flow direction and being configured for being displaceable in response to the pressure such that the length of the patterned section changes in response to the pressure; and
    a pressure detector configured for responding to the displacement of the patterned section by generating a detector signal being indicative of a value of the pressure.

2. The fluidic chip device according to claim 1, comprising:
    a further patterned section of an alternating sequence of further bars and further fluidic channels for conducting a further fluid under pressure, wherein the further patterned section is configured for being displaceable in response to the pressure of the further fluid;
    wherein the pressure detector is configured for responding to the displacement of the further patterned section by generating a further detector signal being indicative of a value of the pressure of the further fluid; and
    a differential pressure determining unit configured for determining information related to a pressure difference between the fluid and the further fluid based on the detector signal and based on the further detector signal.

3. The fluidic chip device according to claim 2, wherein:
    the plurality of layers comprises at least a first layer and a second layer positioned along a stacking direction perpendicular to the resultant flow direction;
    the first layer comprises a first part and a second part positioned along the resultant flow direction;
    the second layer comprises a first part and a second part positioned along the resultant flow direction;
    the patterned section comprises a first sub-section occupying the first part of the first layer, and a second sub-section occupying the second part of the second layer; and
    the further patterned section comprises a first sub-section occupying the first part of the second layer, and a second sub-section occupying the second part of the first layer.

4. The fluidic chip device according to claim 2, comprising one of the following features:
    the patterned section and the further patterned section occupy at least two layers of the plurality of layers, and further comprising an intermediate layer between the at least two layers; or
    the patterned section and the further patterned section occupy at least two layers of the plurality of layers, and the at least two layers are directly adjacent to each other.

5. The fluidic chip device according to claim 2, comprising:
a processing element for processing the fluid supplied at an inlet of the processing element so that the processed fluid is supplied as the further fluid at an outlet of the processing element;
wherein the differential pressure determining unit is configured for determining a pressure drop of the fluid as a result of the processing.

6. The fluidic chip device according to claim 2, wherein the fluidic channels and the further fluidic channels are arranged in corresponding layers of the plurality of layers without overlap in a projection to a plane perpendicular to a stacking direction of the layers.

7. The fluidic chip device according to claim 2, comprising at least one of the following features:
a pressure source for supplying the fluid to the fluidic channels under pressure and comprising a further pressure source for supplying the further fluid to the further fluidic channels under a further pressure; and
a pressure source for supplying the fluid to the fluidic channels under pressure and comprising a further pressure source for supplying the further fluid to the further fluidic channels under a further pressure, wherein the pressure source and the further pressure source are fluidically decoupled from one another.

8. The fluidic chip device according to claim 2, wherein:
the plurality of layers comprises at least a first layer and a second layer positioned along a stacking direction perpendicular to the resultant flow direction;
all of the fluidic channels of the patterned section occupy the first layer; and
all of the further fluidic channels of the further patterned section occupy the second layer.

9. The fluidic chip device according to claim 1, wherein a connection between the patterned section and a rest of the part of the layers comprising the patterned section is weakened by a weakening structure to thereby enable a motion of the patterned section relative to the rest in response to the pressure.

10. The fluidic chip device according to claim 9, further comprising:
a patterned reference section structurally configured as the patterned section but being free of a weakening structure so that the reference section remains spatially fixed in response to the pressure;
a reference signal detector configured for detecting a reference signal of the patterned reference section in response to the pressure; and
a calibration unit configured for calibrating the detector signal based on the reference signal.

11. The fluidic chip device according to claim 10, wherein the calibration unit is configured for at least partially compensating temperature influences in the detector signal by considering the reference signal.

12. The fluidic chip device according to claim 1, wherein the bars of the patterned section form at least one of a meander structure, a spiral structure, and a zig zag structure.

13. The fluidic chip device according to claim 1, wherein at least one of the layers comprises at least one of a metallic material and a plastic material.

14. The fluidic chip device according to claim 1, wherein the pressure detector comprises at least one of the following features:
a strain gauge;
a strain gauge attached to the patterned section or at least partially integrally formed with the patterned section;
a strain gauge comprising an electric signal supply unit configured for applying an electric signal to an electrically conductive structure of the strain gauge, and a response signal analysis unit configured for analyzing a response signal received in response to the applied electric signal for generating the detector signal;
a strain gauge comprising an electric signal supply unit configured for applying an electric signal to an electrically conductive structure of the strain gauge, and a response signal analysis unit configured for analyzing a response signal received in response to the applied electric signal for generating the detector signal, wherein the response signal analysis unit comprises a Wheatstone bridge;
an electromagnetic radiation source configured for irradiating the patterned section, particularly a reflective surface of the bars, with primary electromagnetic radiation, and an electromagnetic radiation detector configured for detecting secondary electromagnetic radiation received from the patterned section in response to the primary electromagnetic radiation for generating the detector signal;
a capacitive pressure detector;
a resistive pressure detector;
a semiconductor pressure detector;
a tunneling pressure detector;
a position-detection based pressure detector.

15. The fluidic chip device according to claim 1, comprising at least one of the following features:
the patterned section is configured for being displaceable in response to the pressure in accordance with an elastic Hooke characteristic;
two of the layers each comprise a patterned section, wherein the two layers are buried within a stack of the plurality of laminated layers and are arranged symmetrically to one another within the stack;
the patterned section comprises a first sub-section and a second sub-section, wherein the fluidic channels of the first sub-section are arranged with a parallel offset relative to the fluidic channels of the second sub-section to be symmetrically arranged with respect to a neutral axis;
the patterned section is configured as a spring bellow.

16. The fluidic chip device according to claim 1, comprising at least one of the following features:
a diagnosis unit configured for diagnosing, based on the detector signal, a functional capability of the fluidic chip device;
a diagnosis unit configured for diagnosing, based on the detector signal, a functional capability of the fluidic chip device, wherein the diagnosis unit is configured for performing the diagnosing based on at least two detector signals relating to at least two different positions within the fluidic chip device;
at least one fluidic interface for supplying or draining a fluid and being in fluid communication with at least a part of the plurality of layers; and
at least one electric interface for conducting an electric signal and being in electric communication with at least a part of the plurality of layers.

17. The fluidic chip device according to claim 1, wherein at least one of the layers of the plurality of layers has a thickness in a range between 25 µm and 300 µm.

18. The fluidic chip device according to claim 1, comprising a processing element communicating with the fluidic channels and configured for interacting with the fluid.

19. The fluidic chip device according to claim 18, comprising at least one of the following features:
- the processing element comprises a fluidic channel for conducting the fluid;
- the processing element comprises a heat exchanger configured for enabling the fluid to exchange heat with another fluid;
- the processing element comprises a flow sensor;
- the processing element comprises a mixing unit configured for mixing the fluid with another fluid;
- the processing element is configured for retaining the fluid being a part a mobile phase and for allowing other components of the mobile phase to pass the processing element;
- the processing element comprises a separation column;
- the processing element comprises a chromatographic column for separating components of the fluid;
- the fluidic chip device is configured to conduct the fluid through the processing element with a high pressure;
- the fluidic chip device is configured to conduct the fluid through the processing element with a pressure of at least 100 bar;
- at least a part of the processing element is filled with a fluid separating material;
- at least a part of the processing element is filled with a fluid separating material, wherein the fluid separating material comprises beads having a size in the range of 1 µm to 50 µm;
- at least a part of the processing element is filled with a fluid separating material, wherein the fluid separating material comprises beads having pores having a size in the range of 0.008 µm to 0.03 µm.

20. The fluidic chip device according to claim 1, comprising at least one of the following features:
- the fluidic chip device is configured as a fluid separation system for separating compounds of the fluid;
- the fluidic chip device is configured as a fluid purification system for purifying the fluid;
- the fluidic chip device is configured to analyze at least one physical, chemical and/or biological parameter of at least one compound of the fluid;
- the fluidic chip device comprises at least one of the group consisting of a detector device, a test device for testing a device under test or a substance, a device for chemical, biological and/or pharmaceutical analysis, a capillary electrophoresis device, a liquid chromatography device, an HPLC device, a gas chromatography device, a gel electrophoresis device, an electronic measurement device, and a mass spectroscopy device;
- the fluidic chip device is configured as a microfluidic chip device;
- the fluidic chip device is configured as a nanofluidic chip device.

21. A method of detecting information indicative of a pressure value of a fluid flowing in a fluidic chip device configured for processing the fluid, the fluidic chip device comprising a plurality of layers laminated to one another and a pressure detector being at least partially integrated within the plurality of layers, wherein at least a part of the layers comprises a patterned section of an alternating sequence of bars and fluidic channels for conducting the fluid under pressure along a resultant flow direction, the patterned section having a length along the resultant flow direction, the method comprising:
- displacing the patterned section in response to a pressure applied by conducting the fluid under the pressure through the fluidic channels, wherein the length of the patterned section changes in response to the pressure; and
- detecting the displacement of the patterned section by generating, by the pressure detector, a detector signal being indicative of a value of the pressure.

* * * * *